United States Patent [19]

Souter

[11] 3,972,925

[45] Aug. 3, 1976

[54] N-PERFLUOROACYL-AMINO ACIDS AND DERIVATIVES THEREOF

[75] Inventor: Rex W. Souter, Indianapolis, Ind.

[73] Assignee: Eli Lilly and Company, Indianapolis, Ind.

[22] Filed: Oct. 29, 1974

[21] Appl. No.: 518,661

[52] U.S. Cl............... 260/544 Y; 260/326.2; 260/340.9; 260/534 R; 260/561 A; 260/561 K
[51] Int. Cl.²........................ C07C 53/34
[58] Field of Search.................. 260/544 Y

[56] References Cited
UNITED STATES PATENTS

| | | | |
|---|---|---|---|
| 3,691,235 | 9/1972 | McCaully et al. | 260/544 Y X |
| 3,742,047 | 6/1973 | Prill | 260/544 Y |
| 3,748,341 | 7/1973 | Kamiya et al. | 260/326.8 |
| 3,803,223 | 4/1974 | Mazur et al. | 260/534 R |

Primary Examiner—Ethel G. Love
Attorney, Agent, or Firm—Charles W. Ashbrook; Everet F. Smith

[57] ABSTRACT

An N-perfluoroacyl-L-α-amino acid is converted to the corresponding acid halide which is useful as a resolving agent for the resolution of racemic amines.

5 Claims, No Drawings

N-PERFLUOROACYL-AMINO ACIDS AND DERIVATIVES THEREOF

BACKGROUND OF THE INVENTION

Separation of racemic mixtures of compounds into the respective enantiomers can be of utmost importance in chemistry, and is especially important in the pharmaceutical field, since the different enantiomers of a biologically active compound may display different pharmacological effects. Gas chromatography has been demonstrated to provide a rapid, sensitive, and efficient method for separating enantiomers. Gas chromatographic separation of the diastereoisomeric N-trifluoroacetyl-L-prolylamide derivatives of asymmetric amines on an achiral stationary phase is known, as discussed for example by Murano, Agr. Biol. Chem. 37 981-988 (1973); Halpern, et al. Chem. Commun., 34 (1966); and F. Wegand, et al. Chem. Ber., 90, (1957). Separations of this type are especially useful as a means of quality control in pharmaceutical manufacturing. In the monitoring of the quality of products by such gas chromatographic techniques, it is important not only to effect complete separation, but also to accomplish the separation in a minimal amount of time. It would therefore be advantageous to have resolving agents which could shorten the time necessary to obtain an effective resolution of enantiomers.

It is an object of this invention to provide certain N-perfluoroacyl-α-amino acid halides which are effective resolving agents for asymmetric amines. The compounds of this invention have the advantage over the heretofore known N-trifluoroacetyl-L-prolyl chloride resolving agent of allowing a more rapid gas chromatographic separation of the diastereoisomers formed by the reaction of the acid halides with certain asymmetric amines.

SUMMARY OF THE INVENTION

This invention provides N-perfluoroacyl-L-α-amino acids and derivatives thereof having the general structural formula

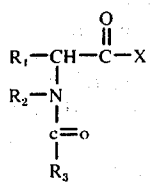

in which $R_1$ is methyl, isopropyl, isobutyl, or together with $R_2$ is $-CH_2CH_2CH_2-$; $R_2$ is hydrogen or together with $R_1$ is $-CH_2CH_2CH_2-$; $R_3$ is trifluoromethyl, pentafluoroethyl, or heptafluoropropyl, but is other than trifluoromethyl when $R_1$ and $R_2$ taken together is $-CH_2CH_2CH_2-$, and is trifluoromethyl when $R_2$ is hydrogen; and X is chlorine, bromine, iodine, or hydroxyl. The compounds of this invention are useful as resolving agents in the resolution of racemic amines. The diastereoisomers formed by reacting an amine with an N-perfluoroacyl-α-amino acid halide of this invention are resolved more rapidly under a given set of chromatographic conditions than the diastereoisomers formed by reaction of an amine with the known trifluoroacetyl-L-prolyl chloride.

DETAILED DESCRIPTION OF THE INVENTION

In accordance with this invention, the foregoing compounds are produced by reacting an L-α-amino acid with a reactive derivative of a perfluoroinated acid, thereby forming the corresponding N-perfluoroacyl-L-α-amino acid. The acylated amino acid thus obtained can be treated with a suitable halogenating agent to provide the corresponding N-perfluoroacyl-L-α-amino acid halide. Some examples of suitable reactive derivatives of perfluorinated acids include the acid halides, such as the acid chloride or acid bromide, the azides, or the anhydrides, including mixed anhydrides. The preferred reactant is a symmetrical acid anhydride. Typical perfluorinated acid anhydrides commonly used include trifluoroacetic anhydride, pentafluoropropionic anhydride, and heptafluorobutyric anhydride. The reaction of the L-α-amino acid and the perfluorinated anhydride, or other reactive derivative of a perfluorinated acid, is generally carried out in the absence of a reaction solvent; however, any of a number of solvents can be incorporated if desired. Suitable solvents that can be used include benzene, dichloromethane, diethyl ether, dioxane, or the like. Typically, however, the perfluorinated anhydride is utilized in an amount sufficient to serve both as reaction solvent and as acylating agent. Normally the anhydride is used in amounts representing about 2 to 100 molar excess of the amino acid; however, more can be used if desired. The reaction is best carried out at a temperature between −10° and 30°C., and at this temperature the acylation is substantially complete within 1 to 3 hours. The N-perfluoroacyl-L-α-amino acid is generally not isolated, but rather the excess anhydride is simply removed, for example by evaporation, and the product is preferably converted directly to an acid halide. Alternatively, the acid can be used as an amine resolving agent by utilizing known reactions to prepare the corresponding diastereoisomers.

Conversion of the aforementioned N-perfluoroacyl-L-α-amino acid to the corresponding acid halide can be accomplished by reaction of the acid with any of a number of commonly used inorganic or organic acid halides. Examples of such halogenating agents include thionyl halides, such as thionyl chloride, thionyl bromide, or thionyl iodide; phosphorus trihalides, such as phosphorus trichloride, or phosphorus tribromide; and organic agents such as oxalyl chloride. The preferred N-perfluoroacyl-L-α-amino acid halides are the acid chlorides, and the preferred chlorinating agent is thionyl chloride. Typically, the N-perfluoroacyl-L-α-amino acid, prepared as described hereinabove, and the halogenating agent, preferably thionyl chloride, are commingled in the absence of a reaction solvent. The halogenating agent is generally used in amounts of about 1 to 25 molar excess of the acylated amino acid, thereby alleviating the need of added reaction solvents. If desired, however, solvents such as benzene, chloroform, diethyl ether, dioxane, or the like, can be incorporated into the reaction. Generally the reaction is carried out at a temperature between −10° and 30°C., and, at this temperature, the reaction is normally complete within about 10 minutes to 3 hours. The product N-perfluoroacyl-L-α-amino acid halide is isolated by simply removing any excess halogenating agent, for example by evaporation, and further purification is generally not needed. The N-acylated amino acid halide thus prepared can, if desired, be dissolved in an organic solvent such as chloroform, dichloromethane, or the like, and stored as a solution for convenient volumetric use. Examples of typical N-perfluoro-L-α-amino acid halides provided by this invention include:
N-trifluoroacetyl-L-alanyl chloride;
N-trifluoroacetyl-L-alanyl bromide;
N-trifluoroacetyl-L-alanyl iodide;
N-trifluoroacetyl-L-valyl chloride;
N-trifluoroacetyl-L-valyl bromide;
N-trifluoroacetyl-L-leucyl chloride;
N-trifluoroacetyl-L-leucyl bromide;
N-pentafluoropropionyl-L-prolyl chloride;
N-heptafluorobutyryl-L-prolyl chloride; and
N-heptafluorobutyryl-L-prolyl bromide.

As hereinbefore indicated, the acid halides of this invention are useful as resolving agents for asymmetric amines. The resolving agents provided herein are superior to the heretofore known N-trifluoroacetyl-L-prolyl chloride since they allow the diastereoisomers formed by reaction of the resolving agent with an amine to be separated more readily than those diastereoisomers prepared from the known resolving agents.

Any of a number of racemic amines can rapidly and efficiently be separated by forming diastereoisomers by reaction with a compound of this invention, and separating the diastereoisomers using a standard gas chromatographic system. Typical racemic amines routinely separated include α-methylbenzylamine, 1-methylhexylamine, α-methylphenethylamine, α-methyl-3,4-(methylenedioxy)-phenethylamine, α-ethylphenethylamine, 1-methyl-3-phenylpropylamine, and the like.

The diastereoisomers which are separated are generally prepared by reaction of a free racemic amine with an acid halide of this invention. Alternatively, the amine can be reacted directly with an acid of this invention, for example in the presence of a coupling reagent such as dicyclohexylcarbodiimide. In the preferred procedure, however, a free racemic amine is treated with an N-perfluoroacyl-L-α-amino acid chloride. The reactants are normally employed in approximately equimolar amounts, although an excess of either can be used if desired. The reaction is generally carried out in a solvent such as chloroform, dichloromethane, ethyl acetate, benzene, or the like. The reaction mixture can contain an added base such as triethylamine if desired to act as an acid binding agent. The reaction is typically conducted at a temperature of about 20° to 30°C., and is generally complete within 30 to 90 minutes. The diastereoisomeric product is generally isolated by washing the reaction mixture with a dilute aqueous base, such as dilute sodium hydroxide for example, and subsequent removal of the reaction solvent.

As hereinbefore indicated, the diastereoisomers so formed are generally separated qualitatively utilizing a gas chromatographic system with an achiral stationary phase. The rapid separation of the diastereoisomers thus accomplished serves as a convenient monitoring of quality control in the production of racemic amines. If desired, the separation of the diastereoisomers can be carried out on larger preparative scales. After separation of the diastereoisomers has been effected, the corresponding free amine can be re-generated by hydrolyzing the pure diastereoisomer, for example by alkaline hydrolysis with sodium hydroxide or the like.

The following table is presented to illustrate the rapid separation of diastereoisomeric amides prepared from a racemic amine and an acid halide of this invention compared to those prepared from an amine and the heretofore known N-trifluoroacetyl-L-prolyl chloride. The separations were carried out under identical gas chromatographic conditions. The indicated time is the time in seconds required for the separation of the diastereoisomers to be effected.

Table I

| Amine being separated | Resolving agent used | Time (Seconds) |
|---|---|---|
| 1-methyl-3-phenylpropylamine | N-trifluoroacetyl-L-prolyl chloride | 1378 |
|  | N-trifluoroacetyl-L-alanyl chloride | 1229 |
|  | N-trifluoroacetyl-L-leucyl chloride | 1066 |
| α-ethylphenethylamine | N-trifluoroacetyl-L-prolyl chloride | 922 |
|  | N-heptafluorobutyryl-L-prolyl chloride | 494 |
|  | N-pentafluoropropionyl-L-prolyl chloride | 595 |
| α-methylphenethylamine | N-trifluoroacetyl-L-prolyl chloride | 3950 |
|  | N-trifluoroacetyl-L-valyl chloride | 2676 |
|  | N-trifluoroacetyl-L-alanyl chloride | 3373 |
| α-methylbenzylamine | N-trifluoroacetyl-L-propyl chloride | 3886 |
|  | N-heptafluorobutyryl-L-prolyl chloride | 2055 |
|  | N-pentafluoropropionyl-L-prolyl chloride | 2273 |

The following detailed examples further illustrate the preparation of the compounds of this invention.

EXAMPLE 1

N-trifluoroacetyl-L-valine

One gram of L-valine was poured into a 125 ml. flask and cooled to 5°C. in an ice-water bath. To the cold L-valine was added in one portion 10 ml. of trifluoroacetic anhydride. The reaction mixture was stirred at 5°C. for 2 hours. The excess trifluoroacetic anhydride was removed under reduced pressure under a stream of dry nitrogen gas, providing N-tirfluoroacetyl-L-valine as an oil.

EXAMPLE 2

N-trifluoroacetyl-L-valyl chloride

A solution of 1 g. of N-trifluoroacetyl-L-valine in 5 ml. of thionyl chloride was cooled to 5°C. and stirred for 15 minutes. The excess thionyl chloride was removed under reduced pressure under a stream of dry nitrogen gas, affording N-trifluoroacetyl-L-valyl chloride as an oil.

EXAMPLES 3-6

The following N-perfluoroacyl amino acid chlorides were prepared from the corresponding N-perfluoroacyl amino acid and thionyl chloride by following the procedure set forth in Example 2.
N-trifluoroacetyl-L-alanyl chloride;
N-trifluoroacetyl-L-leucyl chloride;
N-heptafluorobutyryl-L-prolyl chloride;

N-pentafluoropropionyl-L-prolyl chloride.

I claim:
1. A compound of the formula

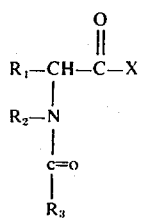

wherein:
$R_1$ is methyl, isopropyl, or isobutyl;
$R_2$ is hydrogen;
$R_3$ is trifluoromethyl, pentafluoroethyl, or heptafluoropropyl; and
X is chlorine, bromine, or iodine.

2. The compound of claim 1 wherein X is chlorine.
3. The compound of claim 2 wherein $R_1$ is methyl.
4. The compound of claim 2 wherein $R_1$ is isopropyl.
5. The compound of claim 2 wherein $R_1$ is isobutyl.